United States Patent [19]

Dunn

[11] Patent Number: 4,521,401

[45] Date of Patent: Jun. 4, 1985

[54] CONSTANT RELEASE RATE SOLID ORAL DOSAGE FORMULATIONS OF QUINIDINE

[75] Inventor: James M. Dunn, Littleton, Colo.

[73] Assignee: Verex Laboratories, Inc., Englewood, Colo.

[21] Appl. No.: 580,933

[22] Filed: Feb. 16, 1984

Related U.S. Application Data

[62] Division of Ser. No. 455,192, Jan. 3, 1983.

[51] Int. Cl.$^3$ ............................ A61K 9/22; A61K 9/26
[52] U.S. Cl. ............................................ 424/19; 424/22
[58] Field of Search ....................................... 424/19–22

[56] References Cited

U.S. PATENT DOCUMENTS 3,577,514  5/1971  Robinson ............................ 424/22

FOREIGN PATENT DOCUMENTS 1538123  1/1979  United Kingdom ................. 424/22

OTHER PUBLICATIONS

Gibson et al., C.A. 97, #133454A, (1982).
Juslin et al., C.A. 96, #40847v, (1982).
Khann et al., C.A. 94, #127301v, (1981).
Jayaswal et al., C.A. 93, #155800e, (1980).
Chasseaud et al., C.A. 85, #68210d, (1976).
Ekenved et al., C.A. 76, #1037562, (1972).
Mahon et al., C.A. 85: 51668m, (1976).
Sawyer et al., C.A. 98: 78054p, (1983).

*Primary Examiner*—Shep K. Rose
*Attorney, Agent, or Firm*—Niblack & Niblack

[57] ABSTRACT

A constant order release rate solid oral dosage formulation of quinidine or a pharmaceutically acceptable salt thereof, said formulation comprising: a therapeutically effective amount of quinidine or a pharmaceutically acceptable salt; from about 0.5 to 6.0 weight percent of an acid-retardant or hydrophobic cellulose derivative; from about 2.5 to 35 weight percent of a hydrogenated vegetable oil: from about 1 to 20 weight percent of an acrylic acid polymer; from about 0.5 to 4.0 weight percent of fumed silicon dioxide and from about 0.4 to 3.0 percent of a lubricant.

8 Claims, No Drawings

CONSTANT RELEASE RATE SOLID ORAL DOSAGE FORMULATIONS OF QUINIDINE

This is a division of application Ser. No. 455,192 filed Jan. 3, 1983.

BACKGROUND OF THE INVENTION

The present invention relates to improved pharmaceutical formulations and more specifically relates to constant release rate solid oral dosage formulations of quinidine or a pharmaceutically acceptable salt thereof.

It is an axiom in pharmaceutical science than in order for a drug in an oral solid dosage formulation to be absorbed, it must first become soluble in the aqueous media of the stomach or small intestine. Products which are rapidly dissolved in water are also rapidly absorbed into the body. For such products, controlling their rate of solvation after ingestion also influences their rate of absorption, and drugs which are highly or moderately water-soluble present special formulation problems.

Formulations which effectively control the rate of solvation of highly water-soluble drugs are disclosed and claimed in commonly assigned, copending U.S. patent applications Ser. No. 443,397, filed Oct. 8, 1982. See also commonly assigned, copending U.S. Pat. applications Ser. No. 364,014 filed Mar. 31, 1982 for constant order release theophylline formulations, allowed U.S. Ser. No. 366,594, filed Apr. 8, 1982 for constant order release aspirin formulations and U.S. Ser. No. 334,124 filed Dec. 24, 1981 for constant release indomethacin formulations. The above commonly assigned, copending application discloses constant order release solid oral dosage formulations which provide a smooth onset of drug action with a subsequent longer duration of pharmacological activity and avoid the peaks and valleys of activity and side effects of drugs administered in conventional formulations, including conventional timed-release formulations. It was also recognized that in view of the number of factors which successfully overcomes the properties peculiar to a specific drug or a group of drugs which share given properties, simply is not suitable for all drugs for the following reasons.

A second factor influencing drug absorption after solubility has occurred is the passage of the drug across the intestinal membrane. A drug generally crosses several membranes to reach its receptor site. This transfer is usually accomplished by passive diffusion. Special transport mechanisms such as facilitated diffusion and active transport allow somes substances to cross cell membranes at a faster rate than simple diffusion. By far, however, the most common mechanism for transport of a drug in solution across the intestinal wall is by passive diffusion.

Passive diffusion is characterized by the movement of the drug molecule down a concentration or electrochemical gradient without the expenditure of cellular energy. The transfer process is neither saturable nor inhibited by other materials and is only slightly sensitive to temperature changes. Since most cells in the gastrointestinal tract are in close proximity to capillaries, the passage of drugs across short distances is usually rapid.

The driving force for passive drug transport is the difference between the concentration of the diffusing drug in the intestinal tract and the concentration gradient of the drug on the other side of the plasma membrane. The rate of drug penetration corresponds to the concentration gradient and is characterized by Fick's law.

Many drugs are either an organic acid or a base. Acids donate a hydrogen ion to form a negatively charged anion, while bases accept a hydrogen ion to form a positively charged cation. It is usually assumed that only nonionized, lipid-soluble drugs pass through the lipid rich membranes of the intestinal tract. The ionized molecule is thought to be too polar to penetrate this lipoidal barrier. If it does cross the cell wall, it does so at a slow rate. This concept of drug absorption is known as nonionic diffussion.

An extension of this theory is the pH partition hypothesis, which asserts that the passage rate of a drug through a membrane is dependent upon the pH of the drug's enviroment and the dissociation constant, or "$pK_a$" of the drug. The $pK_a$ is expressed as the pH at which 50% of the drug will be in the ionized form and 50% will be in the nonionized form. Diffusion of acids and bases across the membrane is not always influenced by pH, as in the case of weak acids or bases. These types of products are essentially completely nonionized at all physiologic pH values. At the other extreme however, are strong acids and bases which are almost completely ionized, and their transfer is dependent upon the pH at which they become dissolved and subsequently become ionized or nonionized.

An example of pH partition hypothesis may be explained by the fact that aspirin, which has a $pk_a$ or dissociation constant of between 3 and 3.7 becomes very nonionized in the acid media of the stomach and subsequently is rapidly absorbed from the gastric mucosa, where the pH is between 1 and 3. As the drug particles pass into the small intestines where the pH increases and the rate of ionization is changed so absorption is subsequently slowed. Conversely strong bases such as ephedrine, which has a $pK_a$ of 9.3, or amphetamine with a $pK_a$ of 9.9 are almost negligibly absorbed from the acidic gastric contents, but are absorbed rather rapidly from the intestinal fluid which has a much lower hydrogen ion concentration. By controlling the release of a drug from the tablet matrix one can control the rate of solvation. The rate of absorbtion for those products having a $pK_a$ above 7 will be greatest, once they reach the small intestine.

While the pH partition hypothesis and nonionic diffusion cannot entirely account for drug absorbtion, however it is one factor to consider among the various factors controlling the rate and mechanism of drug absorbtion in the instestinal tract.

The present invention provides formulations for drugs with a basic nature ie: $pk_a$ 7–10. The formulations of the present invention release their contents in a rather constant manner in the small intestine, thereby controlling the rate at which passive diffusion can occur. While commonly assigned, co-pending U.S. patent application Ser. Nos. 443,497; 364,014; 366,594 and 334,124 disclose various constant release formulations, the present invention provides formulations which take into account the pH partition and which will release basic drugs into the small intestines at a constant and controlled rate, thereby controlling their serum level and prohibiting the peaks and valleys or erratic absorbtion which may be obtained with standard formulations.

SUMMARY

This invention provides constant order formulations of the cardiovascular agent quinidine or a pharmaceutically acceptable salt thereof. Quinidine has a water solubility of 100 gm/ml.

DETAILED DESCRIPTION OF PREFERRED EMBODIMENTS

The present invention provides a constant order release, solid oral dosage formulation of the cardiovascular drug quinidine or a pharmaceutically acceptable salt thereof, said formulation comprising a therapeutically effective amount of said drug, the drug particles being coated with from about 2.5 to about 6 weight percent of an acid-retardant cellulose derivative, preferably from 0.8 to 4.6 weight percent; in a lipid-polymer matrix. The lipid comprises from 2.5 to 35.0 weight percent of the composition, preferably between 7.0–25.0 weight percent. The preferred lipids are hydrogenated vegetable oil and the preferred hydrogenated vegetable oil is a hydrogenated cotton seed oil sold under the mark LUBRITAB by E. Mendell Corporation. The preferred acid polymer is an acrylic acid polymer, carboxypolymethylene (carbomer) sold under the trademark CARBOPOL-934-P by B. F. Goodrich. The acid polymer is present in amounts ranging from 1 to 20 weight percent of the formulation, preferably from about 2.5 to 12 weight percent. The composition of the present invention additionally comprises an anti-sticking agent, preferably fumed silicon dioxide sold under the mark SYLOID-244 by W. Grace Company in amounts of between 0.5–4.0 weight percent of the composition and from 0.4 to 3.0 weight percent of a tabletting lubricant such as magnesium stearate, talc, stearic acid and the like.

The preferred acid-retardant and hydrophobic cellulose derivatives include, but are not limited to, cellulose acetate phthalate, hydroxypropylmethyl cellulose phthalate, ethylcellulose and the like. Such agents are well known in the art.

In addition, the formulations of the present agent may optionally include bulking agents and disintegrants, depending upon the desired release characteristic of the finished product. Such agents are optional, and not critical to the present formulations.

The formulations of this invention retard the release of the active drug in the gastric juices where there is a low pH and subsequently there would be a high degree of nonionized material available, which would result in rapid absorption of the drug product. Controlling the drug release is accomplished by the incorportion of an acid resistant cellulose derivative perferably cellulose actate phthalate or hydroxypropylmethyl cellulose phthalate into the formulation.

The lipid complex component of the present formulation slows the solvation rate of the drug as it enters the more neutral to akaline media of the small intestine. Although there will be a shift in the dissociation constant producing more ionized drug, the incorporation of the drug product into a lipid material offsets the changes in dissociation constant facilitating the absorption of the ionized fragments by the inherent lipophilicity of the solvated material. This lipid content also controls the rate of drug release from the tablet matrix further assuring a controlled and constant release rate product. By utilizing a hydrophosic cellulose derivative the rate of drug dissolution and solvation is also controlled.

It is important to note that compositions containing polymers of acrylic acid in conjunction with hydrogenated vegetable oil 20 are mechanically difficult to press into a tablet without considerable weight variation in the tablets or sticking to the tablet punches. The classical tabletting lubricants such as talc, magnesium stearate, stearic acid, cetyl alcohol, calcium stearate or zinc stearate are ineffective in 25 alleviating this problem. It was found that the only suitable solution to the problem was the inclusion of 0.5 to 4.0 weight percent of fumed silicon dioxide, sold under the trademark SYLOID-244 by W. Grace Company. This both alleviates the problem of tablet sticking and serves as 30 superior lubricant.

Turning to the preferred process of the present invention, all materials are weighed and blended for 15 minutes for each 40 kilograms of dry material. Isopropyl alcohol which may constitute 35–60 weight percent is slowly added at a rate of 3 minutes per liter of solvent. If ethylcellulose is to be dispersed in the solvent prior to granulation, the cellulose derivative should be blended until there is complete dispersion and clarity of the solution. Generally, it will take between 35–40 minutes per 125 liters of fluid using a lightening blender to effect complete dispersion and solvation of the ethylcellulose. It is critical that the wet granulation be completely dried before screening. Failure to observe this technique may result in rupture of the granules and a loss of the constant release rate profile of the resulting tablets. In conventional prior art methods, the wet granulations are generally screened immediately after formation, then dried. If the prior art processes are employed, the constant release rate profile of the tablets may be destroyed.

When cellulose acetate phthalate is employed in formulations of the present invention, it is important to granulate the drug and cellulose acetate phthalate, and/or bulking agent or disintegrant if such agents are employed, with the solvents and subsequently add the remainder of the ingredients. Otherwise, a viscous, rubbery mixture which cannot be tabletted will be obtained.

The following examples further illustrate the present invention.

EXAMPLE 1

Quinidine sulfate tablets weighing 362 mg are prepared from the following formulation:

| | | |
|---|---|---|
| 1. Quinidine Sulfate | 300 | gm |
| 2. Hydrogenated Cotton seed oil | 25 | gm |
| 3. Carbopol - 934p | 10 | gm |
| 4. Microcrystalline cellulose | | |
| 5. Cellulose acetate phthalate | 9 | gm |
| 6. Syloid 244 | 10 | gm |
| 7. Magnesium stearate | 5 | gm |
| 8. Methylene chloride | 25 | ml |
| 9. Isopropyl alcohol | 100 | ml |
| | 362 | gm |

In the above formulation quinidine sulfate, dibasic calcium phosphate, and microcrystalline cellulose are blended in a Hobart mixer. The cellulose acetate phthalate is dissolved in methylene chloride and isopropyl alcohol until a clear solution is achieved. The dry blend is then granulated with the solvent-cellulose solution until a well formed granulate is produced. The product is dried at 100° F. and then passed through a #18 mesh screen blended with magnesium stearate and compressed into capsule-shaped tablets weighing 362 mg, with a hardness of 10–12 kp. These tablets were then placed in a standard U.S.P. disintegration apparatus without discs and a gastric solution with a pH of 1.2–1.4. The amount of mean weight loss in 6 tablets over 3 hours in shown below.

| DISINTEGRATION % pH 1.2–1.4 | | | | |
| --- | --- | --- | --- | --- |
| | 0 HR | 1 HR | 2 HR | 3 HR |
| 1. | 414 mg | 410 | 407 | 400 |
| 2. | 416 mg | 412 | 406 | 398 |
| 3. | 412 mg | 406 | 405 | 399 |
| 4. | 413 mg | 408 | 402 | 392 |
| 5. | 417 mg | 412 | 409 | 389 |
| 6. | 414 mg | 410 | 403 | 395 |
| mean | 414.3 | 409.6 | 405.3 | 395.5 |
| S.D.+ | 1.86 | 2.3 | 2.6 | 4.3 |
| % Loss | 0 | 1.13% | 2.2% | 4.8% |

This demonstrates that after 3 hours of agitation in gastric acid media the tablets lost less than 5% of their weight.

Tablets from this same batch were tested for dissolution using a U.S.P. apparatus II at 50 rpm and pH 7.5. The following are the results from that test expressed as % of drug dissolved:

| DISSOLUTION % OF DRUG DISSOLVED | | | | | |
| --- | --- | --- | --- | --- | --- |
| | 1 HR | 2 HR | 3 HR | 4 HR | 5 HR | 6 HR |
| 1. | 23% | 31% | 42% | 56% | 62% | 75% |
| 2. | 25% | 30% | 43% | 52% | 65% | 73% |
| 3. | 26% | 29% | 44% | 53% | 61% | 76% |
| 4. | 22% | 33% | 46% | 55% | 67% | 77% |
| 5. | 19% | 32% | 41% | 51% | 60% | 74% |
| 6. | 21% | 31% | 40% | 54% | 63% | 72% |
| mean % | 22.7% | 31.0% | 42.7% | 53.5% | 63.0% | 74.5% |
| S.D.+ | 2.58 | 1.40 | 2.16 | 1.87 | 2.61 | 1.87 |

This study demonstrates the behavior of the tablets in a more neutral to akaline media. Using linear regression analysis on the above information, a constant release rate pattern is demonstrated. The correlation coefficent(r value) slope and intercept are shown below.

ANALYSIS BY LINEAR REGRESSION $r = 0.999$ $slope = 0.096$ $intercept = -1.076$

EXAMPLE 2

Quinidine sulfate tablets weighing 430 gm are prepared from the following formulation.

| | | |
| --- | --- | --- |
| 1. Quinidine sulfate | 300 | gm |
| 2. Hydrogenated cotton seed oil | 100 | gm |
| 3. Carbopol-934P | 10 | gm |
| 4. Ethylcellulose (100 cps) | 10 | gm |
| 5. Fumed silicon dioxide | 5 | gm |
| 6. Magnesium stearate | 5 | gm |
| 7. Isopropyl alcohol | 100 | gm |
| | 430 | gm |

The quinidine, hydrogenated cotton seed oil and microcrystalline cellulose are blended. Ethycellulose is dissolved with agitation in isopropyl alcohol. After complete dispersion, the solvent-cellulose solution is used to granulate the quinidine, cottonseed oil and microcrystalline cellulose. After a granulate is formed it is completely dried at 100° F., passed through a #18 mesh screen and compressed into tablets weighing 430 mg containing 300 mg of quinidine sulfate with a hardness of 10–12 kp.

EXAMPLE 3

Hydralazine tablets weighing 580 mg and containing 400 mg of active drug are prepared from the following formulation.

| | | |
| --- | --- | --- |
| 1. Hydralazine hydrochloride | 400 | gm |
| 2. Lactose | 40 | gm |
| 3. Hydrogenated cotton seed oil | 100 | gm |
| 4. Carbopol 934-P | 20 | gm |
| 5. Microcrystalline cellulose | 10 | gm |
| 6. Fumed silicon dioxide | 7 | gm |
| 7. Magnesium stearate | 3 | gm |
| 8. Isopropyl alcohol | 250 | gm |
| | 580 | gm |

Hydralazine, lactose, hydrogenated cottonseed oil Carbopol 934-P and microcrystalline cellulose are placed in a Hobart mixer and throughly blended. A wet granulation is then made by adding slowly the isopropyl alcohol while blending. After a granulate is formed, it is air dried at 100° F. and passed through a number #16–#18 mesh screen and blended with the silicon dioxide and magnesium stearate. Tablets are then compressed from the granulate to form a capsule shaped tablet weighing 580 mg and containing 400 mg of hydralazine. The tablets have a hardness of 10–12 kp.

EXAMPLE 4

Hydralazine tablets weighing 530 mg and containing 200 mg of active drug are prepared from the following formulation.

| | | |
| --- | --- | --- |
| 1. Hydralazine hydrochloride | 200 | gm |
| 2. Lactose | 75 | gm |
| 3. Hydrogenated cotton seed oil | 100 | gm |
| 4. Carbopol 934-p | 20 | gm |
| 5. Cellulose acetate phthalate | 25 | gm |
| 6. Microcrystalline cellulose | 50 | gm |
| 7. Fumed silicon dioxide (Syloid-244) | 6 | gm |
| 8. Magnesium Stearate | 4 | gm |
| 9. Methylene Chloride | 75 | ml |
| 10. Isopropyl alcohol | 150 | ml |
| | 530 | gm |

Hydralazine, lactose, diliasic calcium phosphate, Carbopol 934-P and microcrystalline cellulose are throughly blended in a Hobert mixer. The cellulose acetate phthalate is dissolved in methylene chloride and isopropyl alcohol until a clear solution is obtained, it is then added in a slow steady stream to the blended dry mixture until an overwet granule is formed. The granule is air dried at 100° F. and then passed through a #18 screen, mixed throughly with the silicon dioxide and magnesium stearate. Following this blending the granulate is compressed into tablets weighing 530 mg and containing 200 mg of hydralazine. The tablets have a hardness of 10–12 kp.

Tablets prepared according to the method of example 4 were placed in a USP disintegration apparatus with the fluid media being 1.2–1.4. After 3 hours of agitation there was less than a 10% reduction in tablet weight. Six tablets were randomly selected for dissolution testing in USP apparatus II at 50 r.p.m. and pH 7.5. The following results were observed:

| DISSOLUTION % HYDRALAZINE DISSOLVED | | | | |
|---|---|---|---|---|
| | 1 HR | 2 HR | 3 HR | 4 HR |
| 1. | 20 | 51 | 70 | 93 |
| 2. | 22 | 57 | 76 | 99 |
| 3. | 19 | 49 | 68 | 95 |
| 4. | 24 | 58 | 75 | 98 |
| 5. | 26 | 56 | 73 | 96 |
| 6. | 21 | 54 | 71 | 97 |
| Mean | 22% | 54.2% | 72.2% | 96.3% |
| S.D.+ | 2.61 | 3.54 | 3.06 | 2.16 |

ANALYSIS BY REGRESSION r=0.994
slope=0.041
Intercept=−0.007

EXAMPLE 5

Tablets weighing 488 mg and containing 250 mg of verapamil are prepared from the following formulation.

| | | |
|---|---|---|
| 1. Verapamil hydrochloride | 250 | gm |
| 2. Lactose | 50 | gm |
| 3. Hydrogenated cotton seed oil | 75 | gm |
| 4. Microcrystalline Cellulose | 10 | gm |
| 5. Carbopol 934-P | 70 | gm |
| 6. Ethycellulose (100 cps) | 10 | gm |
| 7. Hydroxypropylmethyl cellulose | 15 | gm |
| 8. Fumed silicon dioxide (Syloid 244) | 5 | gm |
| 9. Magnesium stearate | 3 | gm |
| 10. Isopropyl alcohol | 200 | ml |
| | 488 | |

Ingredients 1-5 are dry blended. Ethycellulose and hydroxypropylmethyl cellulose are disolved in 200 ml isopropyl alcohol and the blended powders are wet granulated. After the granulate is formed it is dried at 100° F. and then passed through a #18 screen, compressed into tablets weighing 488 mg with hardness of 10-12 kp.

EXAMPLE 6

Tablets containing 250 mg of verapmil and weighing 505 mg are prepared for the following formulation.

| | | |
|---|---|---|
| 1. Verapamil hydrochloride | 250 | gm |
| 2. Hydrogentated cotton seed oil | 100 | gm |
| 3. Carbopol 934-p | 70 | gm |
| 4. Lactose | 50 | gm |
| 5. Microcrystalline cellulose | 20 | gm |
| 6. Fumed silicon dioxide | 10 | gm |
| 7. Magnesium stearate | 5 | gm |
| 8. Isopropyl alcohol | 200 | ml |
| | 505 | gm |

Ingredients 1-5 are dry blended in Hobart mixer. Isopropyl alcohol is slowly added to form a wet granulation. The Granulate is then air dried at 100° F., passed through a #16 mesh screen and compressed into tablets weighing 505 mg and containing 250 mg of verapamil, hardness 10-12 kp.

EXAMPLE 7

Verapamil tablets weighing 436 mg and containing 250 g of active drug are prepared from the following formulation.

| | | |
|---|---|---|
| 1. Verapamil hydrochloride | 250 | gm |
| 2. Lactose | 50 | gm |
| 3. Dibasic calcium phosphate | 100 | gm |
| 4. Microcrystalline cellulose | 20 | gm |
| 5. Cellulose acetate phthalate | 10 | gm |
| 6. Syloid - 244 | 3 | gm |
| 7. Talc | 3 | gm |
| 8. Isopropyl Alcohol | 50 | ml |
| 9. Methylene chloride | 50 | ml |
| | 436 | gm |

Ingredients 1-4 are dry blended in Hobart mixer. Cellulose acetate phthalate is dissolved in a mixture of methylene chloride and isopropyl alcohol, after complete dispersion powders are wet granulated with the cellulose mixture. The granules are air dried at 100° F. and passed through #18 screen, blended with stearic acid and talc and compressed into tablets weighing 436 mg and with a hardness of 10-12 kp.

EXAMPLE 8

Tablets containing 250 mg of propranolol and weighing 488 mg are prepared from the following formulation.

| | | |
|---|---|---|
| 1. Propranolol hydrochloride | 250 | gm |
| 2. Hydrogenated cotton seed oil | 50 | gm |
| 3. Lactose | 50 | gm |
| 4. Dibasic calcium phosphate | 75 | gm |
| 5. Microcrystalline Cellulose | 10 | gm |
| 6. Carbopol 934-P | 20 | gm |
| 7. Ethycellulose (100 cps) | 10 | gm |
| 8. Hydroxypropylmethyl cellulose | 15 | gm |
| 9. Fumed silicon dioxide (Syloid 244) | 5 | gm |
| 10. Magnesium stearate | 3 | gm |
| 11. Isopropyl alcohol | 200 | ml |
| | 488 | |

Ingredients 1-6 are dry blended. Ethycellulose and hydroxypropylmethyl cellulose are dissolved in 200 ml isopropyl alcohol and the blended powders are wet granulated. After the granulate has formed, it is dried at 100° F. and then passed through a #18 mesh screen, and compressed into tablets weighing 488 mg with hardness of 10-12 kp.

EXAMPLE 9

Propanolol tablets weighing 505 mg and containing 250 mg of active drug are prepared from the following formulation.

| | | |
|---|---|---|
| 1. Propranolol hydrochloride | 250 | gm |
| 2. Hydrogenated cotton seed oil | 100 | gm |
| 3. Carbopol 934-P | 70 | gm |
| 4. Lactose | 50 | gm |
| 5. Microcrystalline cellulose | 20 | gm |
| 6. Fumed silicon dioxide | 10 | gm |
| 7. Magnesium stearate | 5 | gm |
| 8. Isopropyl alcohol | 200 | gm |
| | 505 | gm |

Ingredients 1-5 are dry blended in a Hobart mixer. Isopropyl alcohol is slowly added to form wet granulation. The granulate is then air dried at 100° F., passed through a #16 mesh screen and compressed into tablets having a hardness at 10-12 kp.

I claim:
1. A constant order release solid oral dosage formulation of quinidine or a pharmaceutically acceptable salt thereof, said formulation comprising: a therapeutically effective amount of quinidine or a pharmaceutically acceptable salt thereof; from about 0.5 to 6.0 weight percent of one or more cellulose derivatives selected from the group consisting of cellulose acetate phthalate, hydroxypropylmethylcellulose, ethyl cellulose, and microcrystalline cellulose; from about 2.5 to 35 weight percent of a hydrogenated vegetable oil; from about 1 to 20 weight percent of carboxypolymethylene; from about 0.5 to 4.0 weight percent of fumed silicon dioxide and from about 0.4 to 3.0 weight percent of a tabletting lubricant.

2. The formulation of claim 1 wherein said cellulose derivative is a combination of cellulose acetate phthalate and microcrystalline cellulose.

3. The formulation of claim 1 wherein said hydrogenated vegetable oil is hydrogenated cottonseed oil.

4. The formulation of claim 1 wherein said cellulose derivative is ethyl cellulose.

5. The formulation of claim 1 wherein said cellulose derivative is a combination of cellulose acetate phthalate and microcrystalline cellulose, and said hydrogenated vegetable oil is hydrogenated cottonseed oil.

6. The formulation of claim 1 wherein said cellulose derivative is ethyl cellulose and said hydrogenated vegetable oil is hydrogenated cottonseed oil.

7. A constant order release solid oral dosage formulation of quinidine or a pharmaceutically acceptable salt thereof comprising: a therapeutically effective amount of quinidine or a pharmaceutically acceptable salt thereof; from 0.5 to 6.0 weight percent of a combination of microcrystalline cellulose and cellulose acetate phthalate; from about 2.5 to 35 weight percent of a hydrogenated vegetable oil; from about 1 to 20 weight percent of carboxypolymethylene; from about 0.5 to 4.0 weight percent of fumed silicon dioxide and from about 0.4 to 3.0 weight percent of a tabletting lubricant.

8. A constant order release solid oral dosage formulation of quinidine or a pharmaceutically acceptable salt thereof comprising: a therapeutically effective amount of quinidine or a pharmaceutically acceptable salt thereof; from 0.5 to 6.0 weight percent of ethyl cellulose; from about 2.5 to 35 weight percent of a hydrogenated vegetable oil; from about 1 to 20 weight percent of carboxypolymethylene; from about 0.5 to 4.0 weight percent of fumed silicon dioxide; and from about 0.4 to 3.0 weight percent of a tabletting lubricant.

* * * * *